United States Patent [19]

Hoornaert et al.

[11] Patent Number: 5,472,967

[45] Date of Patent: Dec. 5, 1995

[54] 4-PYRIMIDINONE DERIVATIVES THEIR PREPARATION AND THEIR APPLICATION IN THERAPY

[75] Inventors: Christian Hoornaert; Marc Daumas; Michel Aletru; Jean-Claude Muller, Morsang Sur Orge, all of France

[73] Assignee: Synthelabo, Le Plessis Robinson, France

[21] Appl. No.: 294,023

[22] Filed: Aug. 24, 1994

Related U.S. Application Data

[63] Continuation of Ser. No. 836,736, Feb. 19, 1992, abandoned, which is a continuation-in-part of Ser. No. 789,269, Nov. 8, 1991, abandoned, which is a continuation-in-part of Ser. No. 659,961, Feb. 26, 1991, abandoned.

[30]     Foreign Application Priority Data

Feb. 20, 1991 [FR] France ..................... 91 02032

[51] Int. Cl.⁶ ..................... C07D 403/10; C07D 239/36; A61K 31/505
[52] U.S. Cl. ..................... 514/269; 544/319; 548/253
[58] Field of Search .................... 544/319; 514/269

[56]                References Cited

U.S. PATENT DOCUMENTS

| | | | |
|---|---|---|---|
| 5,100,897 | 3/1992 | Allen et al. | 544/319 |
| 5,166,206 | 11/1992 | Allen et al. | 544/297 |
| 5,312,828 | 5/1994 | Finkelstein et al. | 514/381 |
| 5,312,920 | 5/1994 | Chekroun et al. | 544/319 |

FOREIGN PATENT DOCUMENTS

| | | |
|---|---|---|
| 253310 | 1/1988 | European Pat. Off. . |
| 291969 | 11/1988 | European Pat. Off. . |
| 323841 | 7/1989 | European Pat. Off. . |
| 401030 | 12/1990 | European Pat. Off. . |
| 400835 | 12/1990 | European Pat. Off. . |
| 400974 | 12/1990 | European Pat. Off. . |
| 407342 | 1/1991 | European Pat. Off. . |
| 424317 | 4/1991 | European Pat. Off. . |
| 15209 | 10/1991 | WIPO . |

OTHER PUBLICATIONS

Koh, E. et al., J. Cardiovascular Pharmacology, 23 (1994) pp. 175–179.

Crabos, M. et al, J. Clin. Invest., 93 (1944), pp. 2372–2378.

Massie, B. M., Cardiovascular Pharmacology and Therapeutics, Ed. B. N. Singh, Churchill Livingstone, N.Y., (1994), pp. 999–1014.

(List continued on next page.)

*Primary Examiner*—Emily Bernhardt
*Attorney, Agent, or Firm*—Jacobson, Price, Holman & Stern

[57]           ABSTRACT

Compounds which can be expressed as tautomeric forms and having the formulas (I), (I') and (I")

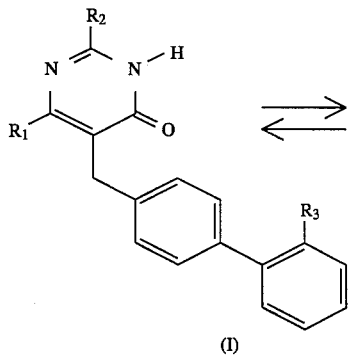

(I)

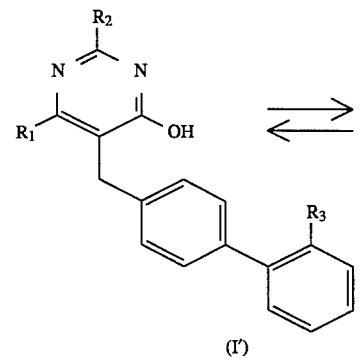

(I')

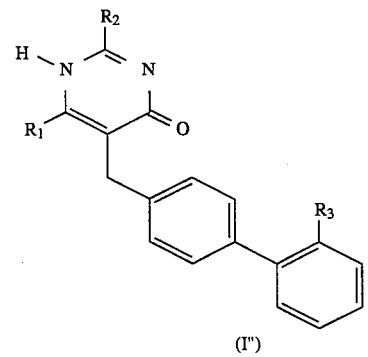

(I")

wherein $R_1$=a straight or branched ($C_{1-7}$) alkyl group or a straight or branched ($C_{3-9}$) alkenyl group or a cyclo($C_{3-7}$)alkyl($C_{1-6}$) alkyl group, $R_2$=an atom of hydrogen, or a straight or branched ($C_{1-7}$)alkyl group, or a cyclo($C_{3-7}$)alkyl($C_{1-3}$)alkyl group, or an aryl($C_{1-3}$)alkyl group optionally substituted on the ring, or an aryloxy($C_{1-3}$)alkyl group optionally substituted on the ring, or an arylthio($C_{1-3}$)alkyl group optionally substituted on the ring, or an arylsulfonyl($C_{1-3}$)alkyl group optionally substituted on the ring, or a heteroaryl($C_{1-3}$)alkyl group optionally substituted on the ring, $R_3$=$CO_2H$, 1H-tetrazol-5-yl, $NHCOR_{11}$, $NHSO_2R_{11}$, $CONHSO_2R_{11}$ or $CONHOR_{12}$ group where $R_{11}$=a methyl, trifluoromethyl, or phenyl group optionally substituted, $R_{12}$=a hydrogen atom, or a methyl or a phenyl group optionally substituted. The compounds are useful for antagonizing angiotensin II.

2 Claims, No Drawings

OTHER PUBLICATIONS

Devereux, R. B. et al, J. Hypertension, 11, Supp. 4. (1993), pp. S3–S9.
B. Roth, "5–Benzyl–2–4–diaminopyrimidines as Antibacterial Agents, I. Synthesis and Antibacterial Activity", Journal of Medicinal and Pharmaceutical Chemistry, vol. 5, No. 6, pp. 1103–1123, Nov. 27, 1962.
Naftilan, A. J. et al, J. Clin. Invest., 83, 1989, p. 1419.
Folkow, B. et al, Circ. Res., 32 (Supp 1), 1973, p. I–2.
Griffin, S. A. et al, Hypertension, 17, 1991, p. 626.
Heagerty, A. M. et al, Lancet, 2, 1988, p. 1209.
Hansson, L., Amer. J. Cardiol., 61, 1988, p. 2C.
Robertson, J. I. S., J. Cardiovasc. Pharmacol., 16(Suppl.7), 1990, p. S102.
Mulvany, M. J. et al, J. Cardiovasc. Pharmacol., 12(Suppl.5), 1988, p. S134.
Schiffrin, E. L. et al, Hypertension, 23, No. 1, 1994, p. 83.
Barenbrock, M. et al, Hypertension, 23, No. 1, 1994, p. I–161.

4-PYRIMIDINONE DERIVATIVES THEIR PREPARATION AND THEIR APPLICATION IN THERAPY

This is a continuation of application Ser. No. 07/836,736, filed Feb. 19, 1992, abandoned, which is a continuation-in-part of application Ser. No. 07/789,269, filed Nov. 8, 1991, abandoned, which is a continuation-in-part of application Ser. No. 07/659,961, filed Feb. 26, 1991, abandoned.

present invention relates to novel substituted 4-pyrimidinone compounds. derivatives thereof, their preparation and their application in therapy.

The compounds of the invention have the formula (I)

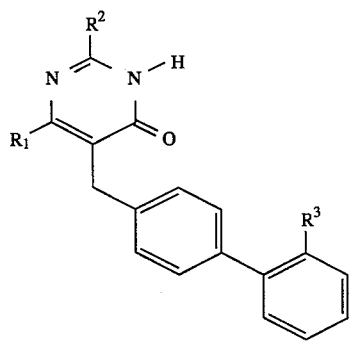

wherein $R_1$ represents either a straight or branched $(C_{1-7})$alkyl group or a straight or branched $(C_{3-9})$alkenyl group or a cyclo$(C_{3-7})$alkyl$(C_{1-6})$alkyl group, $R_2$ represents either an atom of hydrogen, or a straight or branched $(C_{1-7})$alkyl group, or a cyclo$(C_{3-7})$alkyl$(C_{1-3})$alkyl group, or an aryl$(C_{1-3})$alkyl group optionally substituted on the ring, or an aryloxy$(C_{1-3})$alkyl group optionally substituted on the aryloxy$(C_{1-3})$alkyl group optionally substituted on the ring, or an arylsulfonyl$(C_{1-3})$alkyl group optionally substituted on the ring, or a heteroaryl$(C_{1-3})$alkyl group optionally substituted on the ring, $R_3$ is a $CO_2H$, 1H-tetrazol-5-yl, $NHCOR_{11}$, $NHSO_2R_{11}$, $CONHSO_2R_{11}$ or $CCNHOR_{12}$ group where $R_{11}$ represents a methyl, trifluoromethyl, or phenyl group optionally substituted, $R_{12}$ represents a hydrogen atom, or a methyl or a phenyl group optionally substituted.

The preferred compounds of the invention are compounds having the formula (I) wherein, $R_1$ represents a straight or branched $(C_{1-7})$alkyl group, $R_2$ represents a straight or branched $(C_{1-7})$alkyl group, or a cyclo$(C_{3-7})$alkyl$(C_{1-3})$alkyl group, or an aryl$(C_{1-3})$alkyl group optionally substituted on the ring, or a heteroaryl$(C_{1-3})$alkyl group optionally substituted on the ring, $R_3$ is a $CO_2H$ or a 1H-tetrazol-5-yl group.

Among them, the preferred compounds having the formula (I) are those wherein, $R_1$ represents a straight propyl, butyl or pentyl group, $R_2$ represents an arylmethyl, arylethyl, or a heteroarylethyl group, optionally substituted on the ring, $R_3$ is a $CO_2H$ or a 1H-tetrazol-5-yl group.

The most preferred compounds are the compounds having the formula (I) wherein, $R_1$ represents a straight butyl group, $R_2$ represents a benzyl or phenethyl or pyridylethyl or thienylethyl or thiazolylethyl group, optionally substituted on the ring, $R_3$ is a $CO_2H$ or a 1H-tetrazol-5-yl group.

The compounds of choice are those having the formula (I) wherein, $R_1$ represents a straight butyl group, $R_2$ represents a phenylmethyl group, a 4-carboxyphenylmethyl group, a phenylethyl group, 4-methoxyphenylethyl group, a 4- fluorophenylethyl group, a 3,4,5-trimethoxypkenylethyl group, a 3-fluoro-4-methoxyphenylethyl group, a 3-pyridinylethy2. group, a 4-pyridinylethyl group, a 5-(4-methylthiazol)-yl-ethyl group or a 3-thienylethyl group, $R_3$ is a $CO_2H$ or a 1H-tetrazol-5-yl group.

The compounds of formula (I) can be expressed as tautomeric forms

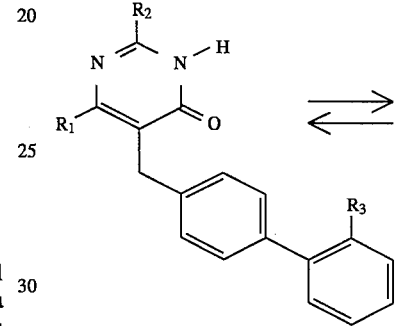

(I)

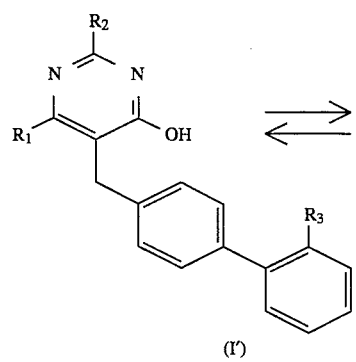

(I')

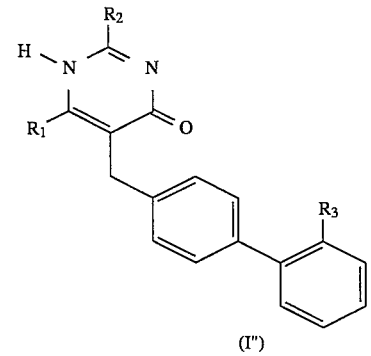

(I")

which are part of the invention.

The compounds of the invention may be present either in a free form or in the form of organic or inorganic pharmaceutically acceptable salts.

The following scheme provides the preparation of the compounds of the invention:

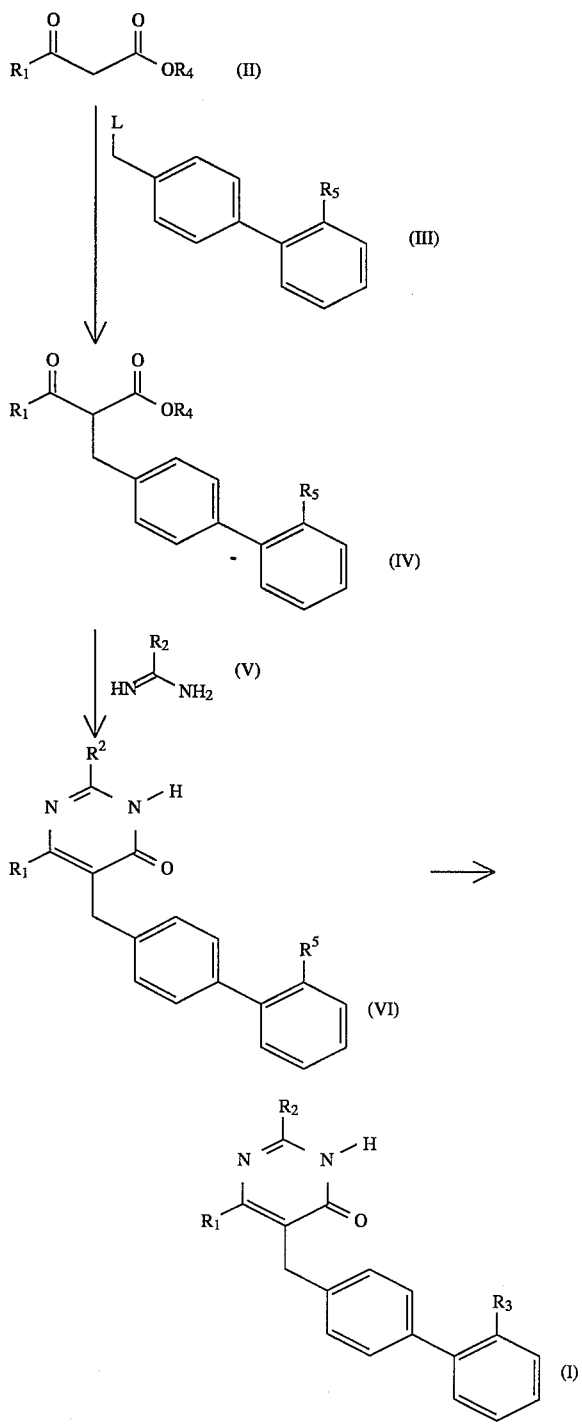

In a first step, a β-ketoester of the general formula (II), in which $R_1$ is as defined above and $R_4$ represents a methyl or ethyl group, is condensed with a derivative of the general formula (III), wherein L represents a leaving group such as chloro, bromo, iodo, p-toluenesulfonyloxy ou methanesulfonyloxy and $R_5$ represents either a carboxylic group $CO_2R_6$, wherein $R_6$ is a methyl, ethyl, 1,1-dimethylethyl or benzyl group, either a nitro group, either a 1H-tetrazol-5-yl group protected, for example, by a triphenylmethyl substituent or 1,1-dimethylethyl substituent, to yield β-ketoester derivatives of the general formula (IV), in which $R_1$, $R_4$ et $R_5$ are as defined above. The derivatives of general formula (III) are described in various European patent applications (253310, 291969, 323841, 400835, 400974, 401030). The reaction is carried out in a solvent such as methanol, ethanol, 1,1-dimethylethanol or dimethylformamide at a temperature between −20° C. and −80° C., in the presence of a base such as sodium hydride, or sodium methylate or potassium 1,1-dimethylethylate and optionally in the presence of a catalyst such as lithium, magnesium or zinc bromide or iodide.

In a second step, a β-ketoester of the general formula (IV) is condensed with an amidine of the general formula (V) to give a pyrimidinone of the general formula (VI), wherein $R_1$, $R_2$ and $R_5$ are as defined above. The reaction is carried out by heating, between 40° C. and 120° C., a mixture of the two compounds, optionally in a solvent such as methanol, ethanol, butanol or toluene, and optionally in the presence of a base such as sodium methylate, potassium carbonate, sodium acetate, pyridine, triethylamine or 4-dimethylaminopyridine.

In a third step, the deprotection and/or the transformation of the group $R_5$ into the group $R_3$ is performed, depending on the nature of the group:

when $R_5$ is a carboxylic ester, the compounds of general formula (VI) are converted, by an acidic or a basic hydrolysis, to the compounds of general formula (I) wherein $R_1$ and $R_2$ are as defined above and $R_3$ is a $CO_2H$ group; the $CO_2H$ group can further be transformed, under classical conditions, by activation by means of various reagents and then by reaction with amines or sulfonamides, to obtain compounds of general formula (I) wherein $R_3$ is a $CONHSO_2R_{11}$ or $CONHOR_{12}$ group and $R_1$, $R_2$, $R_{11}$, $R_{12}$ are as defined above.

when $R_5$ is a triphenylmethyl-1H-tetrazol-5-yl or a 1,1-dimethylethyl-1H-tetrazol-5-yl group, it is deprotected in an acidic medium, under classical conditions, to yield compounds of general formula (I) wherein $R_3$ is the 1H-tetrazol-5-yl group and $R_1$ and $R_2$ are as defined above.

when $R_5$ is a nitro group, it is transformed into an amino group by reduction, to yield the compounds of general formula (VI) which are converted, by acylation or sulfonylation under classical conditions, to compounds of general formula (I) wherein $R_3$ is a $NHCOR_{11}$ or a $NHSO_2R_{11}$ group and $R_1$, $R_2$ and $R_{11}$ are as defined above.

The following examples illustrate the preparation of the compounds of general formula (I). The analysis confirm their structure.

EXAMPLE 1

4'-[(6-butyl-2-ethyl-4-oxo-1,4-dihydro-pyrimidin-5-yl)methyl] [1,1'-biphenyl]-2-carboxylic acid.

1.1. methyl 4'-[(2-methoxycarbonyl)-3-oxoheptyl][1,1'-biphenyl] -2-carboxylate.

To a stirred solution of 16 g of methyl 3-oxo-heptanoate in 145 ml of methanol chilled in an ice bath, a solution of 5.57 g of sodium methylate (prepared from 2.36 g of sodium in 60 ml of methanol) is added. The mixture is stirred at room temperature for 1 hour and then chilled on an ice bath. A solution of 40.12 g of methyl 4'-(bromomethyl)[1,1'-biphenyl] -2-carboxylate in 60 ml of methanol is dropwise added. The mixture is stirred at room temperature for 24 hours. It is concentrated at reduced pressure. The residue is taken up in dichloromethane, washed with an aqueous 1 N solution of hydrochloric acid and then with water. It is dried on sodium sulfate and evaporated in vacuo to obtain 42.4 g of the product, used as such in the following step. 1.2. methyl 4'-[(6-butyl-2-ethyl-4-oxo-1,4-dihydro-pyrimidin-yl) methyl][1,1'-biphenyl]-2-carboxylate. A mixture of 0.48 g of propanimidamide and 2.5 g of the foregoing compound is heated in an argon atmosphere, at 90° C., for 7 hours. The compound is purified by chromatography on silica gel column, eluting with a mixture of dichloromethane and methanol to give 1.1 g of the product in the form of syrup, directly used in the following step.

1.3.4'-[(6-butyl-2-ethyl-4-oxo-1,4-dihydro-pyrimidin-5yl-)methyl] [1,1'-biphenyl]-2-carboxylic.

A solution of 1.1 g of the foregoing compound and 1.4 g of sodium hydroxide is refluxed for 2 hours in a mixture of 30 ml methanol and 3 ml of water. It is concentrated at reduced pressure. The aqueous phase is washed with ether, filtered and acidified with an aqueous 3 N solution of hydrochloric acid. The precipitate is filtered and recristallized in methanol to obtain 0.55 g of the compound in the form of a white powder.

Melting point=207° C.

EXAMPLE 2

4'-[(6-butyl-2-phenylmethyl-4-oxo-1,4-dihydro-pyrimidin-5yl)methyl] [1,1'-biphenyl]-2-carboxylic acid.

Following example 1, a mixture of 0.56 g of benzeneethanimideamide and 1.7 g of methyl 4'-[(2-methoxycarbonyl) -3-oxoheptyl][1,1'-biphenyl]-2-carboxylate is heated at 95° C., under an atmosphere of argon, for 4 hours. The product is purified by chromatography on alumina, by eluting with a mixture of dichloromethane and methanol, to obtain 1.0 g of the product. This product is redissolved in a mixture of 30 ml of methanol and 3 ml of water in the presence of 1.0 g of sodium hydroxide. It is refluxed for 3 hours and concentrated under reduced pressure. The residue is taken up in water. The aqueous phase is washed with ether, filtered and acidified with an aqueous 3 N solution of hydrochloric acid. The precipitate is filtered and recristallized in methanol to obtain 0.60 g of the compound in the form of a white powder.

Melting point=219° C.

EXAMPLE 3

4'-[[6-butyl-2-(2-phenylethyl)-4-oxo-1,4-dihydro-pyrimidin-5yl] methyl][1,1'-biphenyle]-2-carboxyli acid.

Following example 1, a mixture of 1.0 g of benzenepropanimideamide and 2.4 g of methyl 4'-[ (2-methoxycarbonyl)-3-oxoheptyl][1,1'-biphenyl]-2-carboxylate is heated at 95° C., for 6 hours. The product is purified by chromatography on silica gel column, by eluting with a mixture of dichloromethane and methanol, to obtain 1.0 g of the product in the form of a syrup. This product is redissolved in a mixture of 30 ml of methanol and 3 ml of water in the presence of 1.1 g of sodium hydroxide. It is refluxed for 3 hours and concentrated under reduced pressure. The residue is taken up in water. The aqueous phase is washed with ether, filtered and acidified with an aqueous 3 N solution of hydrochloric acid. The precipitate is filtered and recristallized in methanol to obtain 0.60 g of the compound in the form of a white powder.

Melting point=194° C.

EXAMPLE 4

6-butyl-2-(2-phenylethyl)-5-[[2'-(1H-tetrazol-5-Yl)[1,1-biphenyl] -4-yl]methyl]-pyrimidin-4(1H)-one.

4.1. methyl 3-oxo-2-[[2'-(1-triphenylmethyl-1H-tetrazol-5yl)[ 1,1'-biphenyl]-4-yl]methyl]heptanoate. To a solution of 0.97 g of potassium 1,1-dimethylethylate in 15 ml of dimethylformamide, chilled on an ice bath, under an atmosphere of argon, a solution of 1.3 g of methyl 3-oxoheptanoate in 13 ml of dimethylformamide is added, followed by 1.67 g of lithium bromide and a solution of 5 g of 5-[4-(bromomethyl)[ 1,1'-biphenyl]-2-yl]-1-triphenylmethyl-1H-tetrazole in 25 ml of dimethylformamide. The reaction mixture is stirred for 5 hours at room temperature and then diluted with 300 ml of ether. The mixture is washed twice with 100 ml of water and then with 100 ml of a saturated aqueous solution of ammonium chloride. It is dried on magnesium sulfate and evaporated in vacuo to obtain 4.6 g of the product in the form of a yellow oil used as such in the following step.

4.2.6-butyl-2-(2-phenylethyl)-5-[[2'-(1-triphenylmethyl-1H-tetrazol-5-yl) [1,1'-biphenyl]-4-yl]methyl]-pyrimidin-4(1H)one.

A mixture of 0.7 g of benzenepropanimidamide and 3 g of the foregoing compound is heated, under an atmosphere of argon, at 90° C., for 2 hours. The residue is taken up in 120 ml of dichloromethane and the mixture is washed twice with 50 ml of an aqueous 1M solution of potassium carbonate and then with 50 ml of an aqueous 0.1N solution of hydrochloric acid. It is dried on magnesium sulfate and evaporated. The residue is purified by chromatography on silica gel column by eluting with a mixture of dichloromethane and methanol, to obtain 0.85 g of the compound in the form of a whitish foam.

4.3.6-butyl-2-(2-phenylethyl)-5-[[2'-(1H-tetrazol-5yl)[ 1,1'-biphenyl]-4-yl]methyl]-pyrimidin-4(1H)-one. 0.6 g of the foregoing compound is dissolved in a mixture of 5 ml of methanol and 3 ml of diethylether. 2.7 ml of a 1.57 M solution of hydorchloric acid in diethylether are added. The mixture is left at room temperature for 2 hours and then evaporated. The residue is taken up in 70 ml of an aqueous solution of sodium hydroxide. It is washed three times with 30 ml of ether and acidified with hydrochloric acid. The precipitate is filtered and recristallized in methanol to obtain 0.22 g of the compound in the form of a white powder.

Melting point=226–228° C.

EXAMPLE 5

4'-[(2,6-dibutyl-4-oxo-1,4-dihydro-pyrimidin-5yl)methyl] [1,1'-biphenyle]-2-carboxylic acid.

Following example 1, a mixture of 1.1 g of pentanimidamide and 2.5 g of methyl 4'-[(2-methoxycarbonyl)-3-oxoheptyl][ 1,1'-biphenyl]-2-carboxylate is heated at 90° C., under an atmosphere of argon, for 10 hours. The product is purified by chromatography on silica gel column by eluting with a mixture of dichloromethane and methanol, to obtain 1.2 g of product. 1 g of the foregoing product is dissolved in a mixture of 30 ml of methanol and 1 ml of water in the presence of 1.2 g of sodium hydroxide. The mixture is refluxed for 4 hours and concentrated under reduced pressure. The residue is taken up in water. The aqueous phase is washed with ether, filtered and acidified with an aqueous 3 N solution of hydrochloric acid. The precipitate is filtered and recristallized in methanol to obtain 0.45 g of the compound in the form of a white powder.

Melting point=119° C.

EXAMPLE 6

4'-[[6-butyl-2-(3,3'-dimethyl) butyl-4-oxo-1,4-dihydropyrimidin-5-yl]methyl][1,1'-biphenyle]-2-carboxylic acid.

Following example 1, a mixture of 1.3 g of 4,4-dimethylpentanimidamide and 2 g of methyl 4'-[(2-methoxycarbonyl)-3oxoheptyl] [1,1'-biphenyl]-2-carboxylate is heated at 100° C, under an atmosphere of argon, for 8 hours. The product is purified by chromatography on silica gel column by eluting with a mixture of dichloromethane and methanol, to obtain 1.48 g of the product.

The foregoing product is dissolved in a mixture of 60 ml of methanol and 6 ml of water in the presence of 1.67 g of sodium hydroxide. The mixture is refluxed for 6 hours and concentrated under reduced pressure. The residue is taken up in 25 ml of water. The aqueous phase is washed with 25 ml of ether, filtered and acidified with an aqueous 2N solution of hydrochloric acid. The precipitate is filtered, rinsed with water and recrystallized in methanol to obtain 0.6 g of the compound in the form of a white powder.

Melting point=222° C.

EXAMPLE 7

4'-[[6-butyl-2-[2-(thiophen-3-yl)ethyl]-4-oxo-1,4-dihydro-pyrimidin-5-yl] methyl] [1,1'-biphenyl]-2-carboxylic acid.

Following example 1, a mixture of 1.2 g of 3-thiophenpropanimidamide and 2.2 g of methyl 4'-[(2-methoxycarbonyl)-3-oxoheptyl] [1,1'-biphenyl]-2-carboxylate is heated at 110° C., under an atmosphere of argon, for 3.5 hours. The product is purified by chromatography on silica gel column by eluting with a mixture of dichloromethane and methanol, to obtain 0.87 g of the product.

The foregoing product is dissolved in a mixture of 20 ml of methanol and 2 ml of an aqueous 10 N solution of sodium hydroxide. The mixture is refluxed for 3 hours and concentrated under reduced pressure. The residue is taken up in 120 ml of water. The aqueous phase is washed with 3×40 ml of ether, filtered and acidified with an aqueous 6N solution of hydrochloric acid. The precipitate is filtered, rinsed with water and recrystallized in methanol to obtain 0.41 g of the compound.

Melting point=184–185° C.

EXAMPLE 8

4'-[[6-butyl-2-(phenylsulfonyl)methyl-4-oxo-1,4-dihydropyrimidin-5-yl ]methyl][1,1'-biphenyl]-2-carboxylic acid.

Following example 1, a mixture of 2.6 g of 2-phenylsulfonylethanimidamide and 2 g of methyl 4'-[(2-methoxycarbonyl)-3oxoheptyl] [1,1'-biphenyl]-2-carboxylate is heated at 80° C., under an atmosphere of argon, for 6 hours. The product is purified by chromatography on silica gel column by eluting with a mixture of dichloromethane and methanol, to obtain 0.5 g of the product.

The foregoing product is dissolved in a mixture of 15 ml of methanol and 1.5 ml of water containing 0.5 g of sodium hydroxide. The mixture is refluxed for 3.5 hours and concentrated under reduced pressure. The residue is taken up in 150 ml of water. The aqueous phase is washed with 3×80 ml of ether, filtered and acidified with an aqueous 3N solution of hydrochloric acid. The precipitate is filtered, rinsed with water and recrystallized in ethanol to obtain 0.19 g of the compound.

Melting point=210–212° C.

EXAMPLE 9

4'-[[6-butyl-2-(2-chlorophenoxy)methyl-4-oxo-1,4-dihydropyrimidin-5-yl ]methyl][1,1'-biphenyle]-2-carboxylic acid.

Following example 1, a mixture of 1.2 g of 2-(2-chlorophenoxy)ethanimidamide and 2 g of methyl 4'-[(2-methoxycarbonyl)-3-oxoheptyl] [1,1'-biphenyl]-2-carboxylate is heated at 80° C., under an atmosphere of argon, for 4 hours. 0.5 g of 2-(2-chlorophenoxy)ethanimidamide are added twice at 1 hour and 2.5 hours after the beginning of the reaction. The product is purified by chromatography on silica gel column by eluting with a mixture of dichloromethane and methanol, to obtain 0.8 g of the product.

The foregoing product is dissolved in a mixture of 20 ml of methanol and 2 ml of water containing 0.8 g of sodium hydroxide. The mixture is refluxed for 4.5 hours and concentrated under reduced pressure. The residue is taken up in 150 ml of water. The aqueous phase is washed with 3×80 ml of ether, filtered and acidified with an aqueous 3N solution of hydrochloric acid. The precipitate is filtered, rinsed with water and recrystallized in ethanol to obtain 0.29 g of the compound.

Melting point=159–164° C.

EXAMPLE 10

4'-[[6-butyl-2-[2-(4-carboxyphenyl)ethyl]-4-oxo-1,4-dihydropyrimidin-5-yl ]methyl][1,1'-biphenyle]-2-carboxylic acid.

Following example 1, a mixture of 1.4 g of 4-methoxycarbonylbenzenepropanimidamide and 2 g of methyl 4'-[(2-methoxycarbonyl)-3-oxoheptyl] [1,1'-biphenyl]-2-carboxylate is heated at 90° C., under an atmosphere of argon, for 3 hours. The product is purified by chromatography on silica gel column by eluting with a mixture of dichloromethane and methanol, to obtain 1.3 g of the product.

1.1 g of the foregoing product are dissolved in a mixture of 25 ml of methanol and 2 ml of an aqueous 10 N solution of sodium hydroxide. The mixture is refluxed for 3 hours and concentrated under reduced pressure. The residue is taken up in water. The aqueous phase is washed with ether and with ethylacetate. It is acidified with an aqueous solution of hydrochloric acid. The oil is extracted with dichloromethane and the extracts are concentrated. The residue is recristallized in methanol containing a few drops of diisopropylether to obtain 0.37 g of the compound.

Melting point=227° C.

EXAMPLE 11

6-butyl-2-[2-(3,4-methylenedioxyphenyl)ethyl]-5-[[2'-(1H-tetrazol-5-yl) [1,1'-biphenyl]-4-yl]methyl]-pyrimidin-4(1H)one.

Following example 4.2, a mixture of 1,4 g of 3,4-methylene-dioxybenzenepropanimidamide and 2.6 g of methyl 3-oxo-2-[[2-( 1-triphenylmethyl-1H-tetrazol-5-yl)[1,1'-biphenyl]-4-yl] methyl]heptanoate in 3 ml of toluene is refluxed for 4 hours. It is evaporated under vacuum and the product is purified by chromatography on silica gel column by eluting with a mixture of dichloromethane and methanol, to obtain 1 g of the product.

The foregoing product is dissolved in a mixture of 15 ml of methanol and 5 ml of tetrahydrofuran containing I ml of acetic acid. The solution is refluxed for 5 hours and evaporated under vacuum. The residue is triturated with ether. The precipitate is filtered and rinsed with 3×30 ml of ether to obtain 0.45 g of the compound.

Melting point=230–232° C.

EXAMPLE 12

6-butyl-2-[2-(napht-2-yl)ethyl]-5-[[2'-(1H-tetrazol-5yl)[1,1'-biphenyl]-4-yl]methyl]-pyrimidin-4(1H)-one.

Following example 4.2, a mixture of 1.75 g of 3-(napht-2yl)propanimidamide and 3.3 g of methyl 3-oxo-2-[[2'-(1-[1,1-dimethylethyl] -1H-tetrazol-5-yl)[1,1'-biphenyl]-4-yl]methyl]heptanoate is heated at 100° C., for 3.50 hours. The product is purified by chromatography on silica gel column by eluting with a mixture of dichloromethane and methanol, to obtain 2.9 g of the product in the form of a pale yellow paste. 1.5 g of the foregoing product are dissolved in a 30% solution of bromhydric acid in acetic acid. It is heated at 90° C., for 5 hours and evaporated under vacuum. The residue is taken up with dichloromethane. The organic phase is washed with water and dried on sodium sulfate. The solvent is evaporated to give 1.1 of the product in the form of a beige powder. The crude product is purified by chromatography on silica gel column by eluting with a mixture of dichloromethane and methanol, to obtain 0.63 g of the product in the form of a white powder.

Melting point=163–166° C.

The following table illustrates the structures and physical properties of some compounds according to the invention.

TABLE

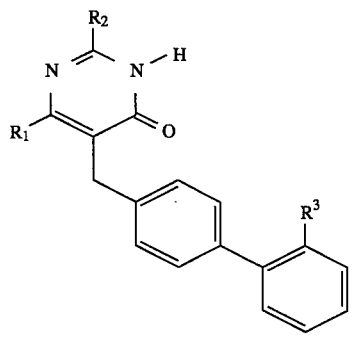

| Compound | $R_1$ | $R_2$ | $R_3$ | Melting point (°C.) |
|---|---|---|---|---|
| 1 | $C_4H_9$ | $CH_3-$ | $CO_2H$ | 217 |
| 2 | $C_4H_9$ | $C_2H_5-$ | $CO_2H$ | 207 |
| 3 | $C_4H_9$ | $C_6H_5-$ | $CO_2H$ | 259 |
| 4 | $C_4H_9$ | $C_6H_5-CH_2-$ | $CO_2H$ | 219 |
| 5 | $C_4H_9$ | $C_6H_5-(CH_2)_2-$ | $CO_2H$ | 194 |
| 6 | $C_4H_9$ | $C_6H_5-(CH_2)_2-$ | 1H-tetrazol-5-yl | 226–228 |
| 7 | $C_4H_9$ | $C_6H_5-CH_2-$ | 1H-tetrazol-5-yl | 226–228 |
| 8 | $C_4H_9$ | $4\text{-}Cl-C_6H_4-CH_2-$ | $CO_2H$ | 230 |
| 9 | $C_4H_9$ | $3\text{-}CH_3O-C_6H_4-CH_2-$ | $CO_2H$ | 177 |
| 10 | $C_4H_9$ | $C_6H_5-(CH_2)_3-$ | $CO_2H$ | 149 |
| 11 | $C_4H_9$ | $C_4H_9-$ | $CO_2H$ | 119 |
| 12 | $C_4H_9$ | $(CH_3)_2-(CH_2)_2-$ | $CO_2H$ | 130 |
| 13 | $C_4H_9$ | $(CH_3)_3-C-(CH_2)_2-$ | $CO_2H$ | 222 |
| 14 | $C_4H_9$ | $\underline{c}\text{-}C_5H_9-(CH_2)_2-$ | $CO_2H$ | 159 |
| 15 | $C_4H_9$ | $\underline{c}\text{-}C_6H_{11}-(CH_2)_2-$ | $CO_2H$ | 205 |
| 16 | $C_4H_9$ | $3\text{-}Cl-C_6H_4-CH_2-$ | $CO_2H$ | 186 |
| 17 | $C_4H_9$ | naphtyl-1-$CH_2-$ | $CO_2H$ | 235 |
| 18 | $CH_3$ | $C_6H_5(CH_2)_2-$ | $CO_2H$ | 265–267 |
| 19 | $C_2H_5$ | $C_6H_5(CH_2)_2-$ | $CO_2H$ | 207–208 |
| 20 | $C_3H_7$ | $C_6H_5(CH_2)_2-$ | $CO_2H$ | 206–207 |
| 21 | $\underline{c}\text{-}C_5H_9-(CH_2)_2$ | $C_6H_5(CH_2)_2-$ | $CO_2H$ | 189–190 |
| 22 | $\underline{C}_5H_{11}$ | $C_6H_5(CH_2)_2-$ | $CO_2H$ | 178–179 |
| 23 | $C_4H_9$ | thienyl-2-$(CH_2)_2-$ | $CO_2H$ | 192–193 |
| 24 | $C_4H_9$ | thienyl-3-$(CH_2)_2-$ | $CO_2H$ | 184–185 |
| 25 | $C_4H_9$ | $C_6H_5-OCH_2-$ | $CO_2H$ | 228 |
| 26 | $C_4H_9$ | $C_6H_5-SCH_2-$ | $CO_2H$ | 152 |
| 27 | $C_4H_9$ | $C_6H_5-SO_2CH_2-$ | $CO_2H$ | 210–212 |
| 28 | $C_4H_9$ | $4\text{-}Cl-C_6H_4-OCH_2-$ | $CO_2H$ | 252–256 |
| 29 | $C_4H_9$ | $3\text{-}Cl-C_6H_4-OCH_2-$ | $CO_2H$ | 227–232 |
| 30 | $C_4H_9$ | $2\text{-}Cl-C_6H_4-OCH_2-$ | $CO_2H$ | 159–164 |
| 31 | $C_4H_9$ | $4\text{-}CH_3O-C_6H_4-OCH_2-$ | $CO_2H$ | 214–219 |
| 32 | $C_4H_9$ | $3\text{-}CH_3O-C_6H_4-OCH_2-$ | $CO_2H$ | 209–212 |
| 33 | $C_4H_9$ | $4\text{-}HO_2C-C_6H_4-OCH_2-$ | $CO_2H$ | 265–268 |
| 34 | $C_4H_9$ | $3\text{-}HO_2C-C_6H_4-OCH_2-$ | $CO_2H$ | >270 |
| 35 | $C_4H_9$ | $4\text{-}CH_3-C_6H_4-(CH_2)_2-$ | $CO_2H$ | 107 |
| 36 | $C_4H_9$ | $4\text{-}CH_3O-C_6H_4-(CH_2)_2-$ | $CO_2H$ | 113 |
| 37 | $C_4H_9$ | $3,4\text{-}OCH_2O-C_6H_4-(CH_2)_2-$ | $CO_2H$ | 213 |
| 38 | $C_4H_9$ | $4\text{-}HOC-C_6H_4-(CH_2)_2-$ | $CO_2H$ | 227 |
| 39 | $C_4H_9$ | $4\text{-}CH_3O-C_6H_4-(CH_2)_2-$ | 1H-tetrazol-5-yl | 194–198 |
| 40 | $C_4H_9$ | $3,4\text{-}OCH_2O-C_6H_4-(CH_2)_2-$ | 1H-tetrazol-5-yl | 230–232 |
| 41 | $C_4H_9$ | $4\text{-}F-C_6H_4-(CH_2)_2-$ | 1H-tetrazol-5-yl | 198–203 |
| 42 | $C_4H_9$ | $3\text{-}F-C_6H_4-(CH_2)_2-$ | 1H-tetrazol-5-yl | 234–236 |
| 43 | $C_4H_9$ | $3,4\text{-}F_2-C_6H_3-(CH_2)_2-$ | 1H-tetrazol-5-yl | 228–230 |

TABLE-continued

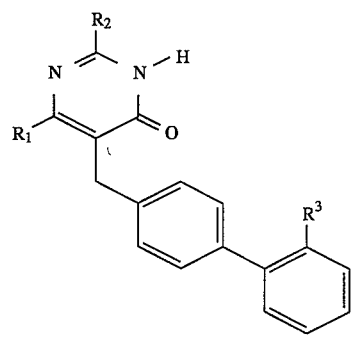

| Compound | R₁ | R₂ | R₃ | Melting point (°C.) |
|---|---|---|---|---|
| 44 | C₄H₉ | 4-CH₃S—C₆H₄—(CH₂)₂— | 1H-tetrazol-5-yl | 190–194 |
| 45 | C₄H₉ | naphtyl-2-(CH₂)₂— | CO₂H | 222–223 |
| 46 | C₄H₉ | naphtyl-1-(CH₂)₂— | CO₂H | 185–186 |
| 47 | C₄H₉ | 3,4-(CH₃O)₂—C₆H₃—(CH₂)₂— | 1H-tetrazol-5-yl | 178–180 |
| 48 | C₄H₉ | 3-CH₃O—C₆H₄—(CH₂)₂— | 1H-tetrazol-5-yl | 226–229 |
| 49 | C₄H₉ | 3,4,5-(CH₃O)₃—C₆H₅—(CH₂)₂— | 1H-tetrazol-5-yl | 198–200 |
| 50 | C₄H₉ | 3-CF₃—C₆H₄—(CH₂)₂— | 1H-tetrazol-5-yl | 209–210 |
| 51 | C₄H₉ | 4-Cl—C₆H₄—(CH₂)₂— | 1H-tetrazol-5-yl | 217–218 |
| 52 | C₄H₉ | 4-CF₃—C₆H₄—(CH₂)₂— | 1H-tetrazol-5-yl | 230–231 |
| 53 | C₄H₉ | 2,4-(CH₃O)₂—C₆H₃—(CH₂)₂— | 1H-tetrazol-5-yl | 205–208 |
| 54 | C₄H₉ | 3-Cl—C₆H₄—(CH₂)₂— | 1H-tetrazol-5-yl | 225–226 |
| 55 | C₄H₉ | pyridinyl-3-(CH₂)₂— | 1H-tetrazol-5-yl | 174–178 |
| 56 | C₄H₉ | pyridinyl-4-(CH₂)₂— | 1H-tetrazol-5-yl | 239–241 |
| 57 | C₄H₉ | 3-F,4-CH₃O—C₆H₃—(CH₂)₂— | 1H-tetrazol-5-yl | 213–214 |
| 58 | C₄H₉ | 4-HO₂C—C₆H₄—CH₂— | 1H-tetrazol-5-yl | 272–275 |
| 59 | C₄H₉ | 3-HO₂C—C₆H₄—CH₂— | 1H-tetrazol-5-yl | 232–233 |
| 60 | C₄H₉ | 4-CH₃SO—C₆H₄—(CH₂)₂— | 1H-tetrazol-5-yl | 195–196 |
| 61 | C₄H₉ | 4-CH₃SO—C₆H₄—(CH₂)₂— | 1H-tetrazol-5-yl | 205–215 |
| 62 | C₄H₉ | 3,5-(CH₃O)₂—C₆H₃—(CH₂)₂— | 1H-tetrazol-5-yl | 205–215 |
| 63 | C₄H₉ | (4-methylthiazol)-5-yl-(CH₂)₂— | 1H-tetrazol-5-yl | 171–174 |
| 64 | C₄H₉ | C₆H₅—(CH₂)₃— | 1H-tetrazol-5-yl | 185–190 |
| 65 | C₄H₉ | CH₃— | 1H-tetrazol-5-yl | 236–237 |
| 66 | C₄H₉ | napthyl-2-(CH₂)₂— | 1H-tetrazol-5-yl | 163–166 |

The compounds of the invention have been the subject of pharmacological studies which have demonstrated their antagonistic properties to angiotensin II.

Test of binding of [³H]-angiotensin II to rabbit adrenal cortex.

Male Fauves de Bourgogne rabbits (2–3 kg body weight) are used. Rabbits are sacrificed by cervical dislocation, the adrenal gland excised and the cortex rapidly dissected at 4° C. Tissues are homogenized in 10 ml of ice-cold 10 mM tris(hydroxymethyl)aminomethane buffer solution, containing 0.33 M sucrose and 1 mM ethylenediaminetetraacetic acid, adjusted to pH 7.4 with hydrochloric acid, in an electrical Potter apparatus at a speed of 1200 revolutions per minute. The volume of the preparation is adjusted to 25 ml with tris-sucrose buffer, before centrifuging for 15 min at 1075 g. The supernatant is kept, the pellet is rehomogenized in 10 ml of tris-sucrose buffer and centrifuged as described above. Both supernatants are pooled and centrifuged for 30 min at 47 800 g. The resulting pellet is resuspended in 150 volumes (i.e. 100 mg of tissue in 15 ml of buffer) of an incubation buffer containing 50 mM tris-HCl, 150 mM NaCl, 5 mM ethylene-diaminetetraacetic acid, 1.25 µg/ml bacitracin, 100 µM phenylmethylsulfonylfluoride and 0.2% bovine serum albumin (pH=7.4 at 25° C.).

Corticoadrenal microsomes (100 µl of suspension) are incubated in the presence of 2 nM [³H]-angiotensin II (New England Nuclear, specific activity 61Ci/mmol) in a final volume of 0.5 ml of incubation buffer for 30 min at 25° C. Following incubation, the microsomes are harvested by filtration on 0.45 µm Millipore HAWP™ cellulose nitrate filters, pretreated with bovine serum albumin, and washed using three 5 ml aliquots of ice-cold tris-HCl buffer. Membrane bound radioactivity retained by the filters is quantified using liquid scintillation spectrometry. Specific [³H]-angiotensin II binding is defined as the amount of filter-retained radioactivity that could be inhibited by incubation in the presence of 1 µM of unlabelled angiotensin .II. It represents 90 to 95% of the total amount of filter-retained radioactivity.

Specific [³H]-angiotensin II binding is measured in the presence of various concentrations of the test compounds and the IC₅₀, the concentration of the test compound which inhibits 50% of specific [³H]-angiotensin II binding, is graphically determined.

The IC₅₀ values of the compounds of the invention are between 5 nM and 10 µM.

Inhibition of pressor response to angiotensin II in rat.

Male Sprague-Dawley rats (250–280 g body weight; Charles River France) are anesthetized with sodium pentobarbital (55 mg/kg i.p.) and maintained under artificial respiration (Harvard™ respirator; rate 70 ml per minute, volume of air 1 ml per 100 g body weight). The animals are pithed through the orbit of the right eye with a metal rod. The right and left vagus nerves are sectioned (bivagotomy); the right carotid artery is ligatured, the left carotid artery being catheterized in order to measure the blood pressure using a pressure cell (Statham™ P23Db type). A femoral vein is catheterized for i.v. administration of drug. Blood pressure is measured after i.v. administration of 0.5 µg/kg angiotensin II. Compounds of the invention or saline vehicle are administered 5 min (for i.v. studies) or 60 min (for p.o. studies) before injection of angiotensin II. The compounds of the invention are administered at doses ranging from 0.01 to 100 mg/kg.

The percentage inhibition of the control response to angiotensin II is used to evaluate the antagonistic potential of the compounds of the invention to angiotensin II.

A compound of the invention has been the subject of a test to determine the antiproliferative effect on vascular smooth muscle cells from normotensive rat aorta (AEV).

The role of angiotensin II as a growth factor in vascular smooth muscle is well established (Naftilan, A.J. et al, *J. Clin. Invest.*, 83, 1989, p. 1419). This action of angiotensin II results in undesirable structural modifications of the vascular wall (hyperplasia, hypertrophy) which, by increasing vascular resistance and reducing arterial compliance, contribute to the development of arterial hypertension (Folkow, B. et al, *Circ. Res.* 32 (Supp 1), 1973, p. I-2; Griffin, S. A. et al, *Hypertension*, 17, 1991, p. 626). Hence, inhibition of angiotensin-induced smooth muscle proliferation is a useful property for the treatment of hypertension.

There are a number of publications which confirm that such structural modification of the vascular wall is known and an important factor relevant to current and future therapy of arterial hypertension in man. These publications (Heagerty, A.M. et al, *Lancet*, 2, 1988, p. 1209; Hansson, L., *Amer. J. Cardiol.*, 61, 1988, p. 2C; Robertson, J.I.S., *J. Cardiovasc. Pharmacol.*, 16(Suppl.7), 1990, p. S102; Mulvany, M. J. et al, *J. Cardiovasc. Pharmacol.*, 12(Suppl.5), 1988, p. S134; Schiffrin, E. L. et al, *Hypertension*, 23, No. 1, 1994, p. 83; Barenbrock, M. et al, *Hypertension*, 23, No. 1, 1994, p. I-161) collectively demonstrate the following:

(i) Structural modifications of the vascular wall are an undesirable feature of hypertension. They could contribute to the condition itself and to the associated cardiovascular sequelae;

(ii) The ability of currently available antihypertensive drugs to reverse these vascular structural changes has been studied. The results are variable and, often, complete regression cannot be achieved;

(iii) The mortality of hypertensives whose blood pressure has been treated continues to be higher than an equivalent normotensive population. Hence, existing antihypertensive therapy is not optimal. It is considered that this excessive mortality may be linked to incomplete reversal of adverse structural cardiovascular modifications; and (iv) New treatments for hypertension are needed which, in addition to lowering blood pressure, reverse the associated structural modifications of the vascular wall.

Therefore, antiproliferative properties of new anti-hypertensive drugs represent a valuable tool in the treatment of this pathology.

Antiproliferative Effects on Vascular Smooth Muscle Cells from Normotensive Rat Aorta Thoracic aortic smooth muscle cells are isolated from 11 week old Wistar Kyoto rats and cultured in multiwell plates. Quiescence is induced by replacing culture medium with Dulbecco's Modified Eagle's Medium mix HAM's F12 supplemented with insulin (1 µM), transferrin (5 µg/ml) and ascorbic acid (100 µM). Quiescent cells are preincubated for 20 h with 3 nM angiotensin II (concentration causing 50% of maximal effect on DNA synthesis) before addition of [$^3$H]-thymidine (0.5 µCi/well) for a 4 h incubation period in the continuing presence of angiotensin II. Compound No. 6 was incorporated at various concentrations one hour before angiotensin II.

At the end of the incubation, cells are washed twice with phosphate buffered saline, and [$^3$H]-DNA is precipitated with ice cold trichloracetic acid (10%), solubilized in sodium hydroxide (0.5M) and quantified by liquid scintillation counting.

$IC_{50}$ which is the concentration of the test compound which inhibits 50% of angiotensin II-induced [$^3$H]-thymidine incorporation (an index of smooth muscle cell proliferation) is calculated by means of non-linear regression using the logistic equation. The $IC_{50}$ value of Compound No. 6 was 0.4

The compounds of the invention or their suitable salts may be used for the treatment of various forms of hypertensive pathologies and of coronary, cardiac, renal or pulmonary insufficiencies as well as for the treatment of glaucoma.

The compounds of the invention or their suitable salts may also be used in combination with other substances possessing cardiovascular activity such as diuretics, α-blockers, β-blockers, calcium antagonists or angiotensine I converting enzyme inhibitors.

The compounds of the invention or their suitable salts may be provided in any pharmaceutical form suitable for treatment by oral, parenteral, intramuscular or rectal administration: tablets, capsules, hard gelatin capsules, sterile solutions or suspensions, suppositories etc.. For the treatment of glaucoma, the compounds of the invention or their suitable salts may be provided in the form of tablets, hard gelatin capsules, injectable solutions or topical ocular formulations.

The compositions of the invention may be administered to patients in an amount which may range from 1 to 1000 mg per day and per patient, in one or more doses.

We claim:

1. A compound with three tautomeric forms, having the formulas (I), (I') and (I")

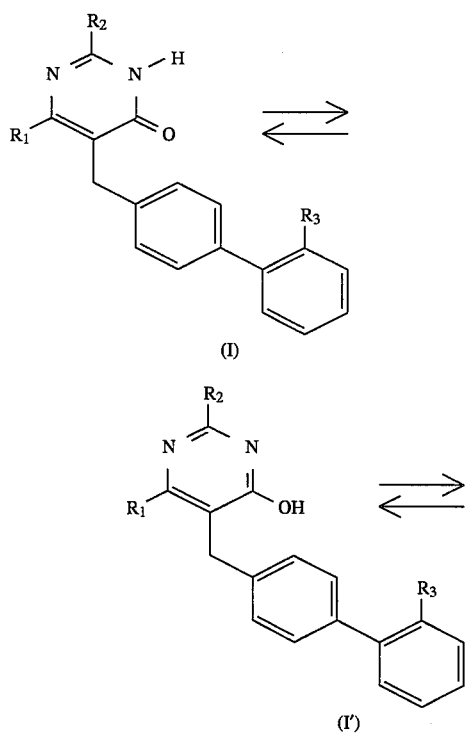

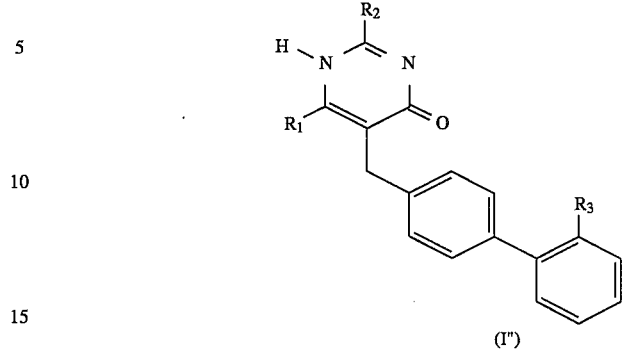

wherein
- $R_1$ is a straight butyl group,
- $R_2$ is a phenylethyl group, and
- $R_3$ is a 1H-tetrazol-5-yl group, or an organic or inorganic pharmaceutically acceptable salt thereof.

2. A pharmaceutical composition useful as an angiotensin II antagonist, comprising a therapeutically effective amount of a compound defined by claim 1, in association with a pharmaceutically acceptable carrier.

* * * * *